United States Patent
Maeda et al.

(10) Patent No.: US 9,962,126 B2
(45) Date of Patent: May 8, 2018

(54) SIGNAL PROCESSOR, SIGNAL PROCESSING METHOD, AND RECORDING MEDIUM

(71) Applicant: FUJITSU LIMITED, Kawasaki-shi, Kanagawa (JP)

(72) Inventors: Kazuho Maeda, Kawasaki (JP); Masato Sakata, Isehara (JP); Daisuke Uchida, Atsugi (JP); Akihiro Inomata, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 1006 days.

(21) Appl. No.: 14/099,457

(22) Filed: Dec. 6, 2013

(65) Prior Publication Data
US 2014/0276114 A1 Sep. 18, 2014

(30) Foreign Application Priority Data
Mar. 15, 2013 (JP) ................................ 2013-054165

(51) Int. Cl.
*A61B 5/00* (2006.01)
*A61B 5/024* (2006.01)

(52) U.S. Cl.
CPC .......... *A61B 5/7246* (2013.01); *A61B 5/0077* (2013.01); *A61B 5/0082* (2013.01); *A61B 5/024* (2013.01)

(58) Field of Classification Search
CPC .................................................. A61B 5/0077
USPC ........................................................ 702/189
See application file for complete search history.

(56) References Cited

U.S. PATENT DOCUMENTS

| 6,511,436 | B1 * | 1/2003 | Asmar | A61B 5/021 600/481 |
| 2008/0004904 | A1 | 1/2008 | Tran | |
| 2009/0299154 | A1 | 12/2009 | Segman | |
| 2010/0152600 | A1 | 6/2010 | Droitcour et al. | |
| 2012/0078123 | A1 * | 3/2012 | Futatsuyama | A61B 5/02125 600/485 |
| 2012/0253212 | A1 * | 10/2012 | Maeno | A61B 5/0051 600/508 |
| 2014/0073869 | A1 * | 3/2014 | Rodriguez-Llorente | A61B 5/7246 600/301 |
| 2014/0249432 | A1 * | 9/2014 | Banet | A61B 5/01 600/485 |

FOREIGN PATENT DOCUMENTS

| JP | 9-84776 A | 3/1997 |
| JP | 2012-239474 | 12/2012 |

OTHER PUBLICATIONS

Extended European Search Report of EP Patent Application 13197941.1 dated Apr. 10, 2014, 7 pages.
EPOA—European Office Action dated Feb. 24, 2016 for corresponding European Patent Application No. 13197941.1.
EPOA—European Office Action dated Nov. 10, 2016 for European Patent Application No. 13197941.1.

* cited by examiner

*Primary Examiner* — Ricky Ngon
(74) *Attorney, Agent, or Firm* — Fujitsu Patent Center

(57) ABSTRACT

A pulse wave detection apparatus detects a signal, and calculates a correlation coefficient between waveforms of the signal included in a first window and a second window having a predetermined duration, the correlation coefficient being smaller when a difference between dispersion of the amplitude value in the first window and dispersion of the amplitude value in the second window becomes larger.

6 Claims, 11 Drawing Sheets

SIGNAL PROCESSOR, SIGNAL PROCESSING METHOD, AND RECORDING MEDIUM

CROSS-REFERENCE TO RELATED APPLICATION

This application is based upon and claims the benefit of priority of the prior Japanese Patent Application No. 2013-054165, filed on Mar. 15, 2013, the entire contents of which are incorporated herein by reference.

FIELD

The embodiments discussed herein are related to a signal processor, a signal processing method, and a signal processing program.

BACKGROUND

Correlation coefficients may be used for determining whether waveforms of signal or signals have similarity to each other. Heartbeat measuring devices adopt such a technology for calculating correlation coefficients. The heartbeat measuring device measures the interval of heartbeats of an operator based on electrocardiographic signals. The electrocardiographic signals are measured using a first electrode and a second electrode provided on a handle of a vehicle corresponding to the right and left hands of the operator thereon, and a reference electrode for measuring a reference potential.

In the above-described heartbeat measuring device, the grip pattern of the handle is determined using the correlation coefficient when correcting the time of the peak of the amplitude detected from the electrocardiographic signals. Specifically, the heartbeat measuring device calculates the correlation coefficient between a waveform of an electrocardiographic signal registered for each grip pattern and an electrocardiographic signal, thereby obtaining the similarity of the waveforms. Accordingly, the time of the peak of the amplitude is corrected based on the correction amount associated with the grip pattern of the waveform having the maximum similarity to the registered waveform of the electrocardiographic signal.

Patent Document 1

Japanese Laid-open Patent Publication No. 2012-239474

With the above-described technology, however, the waveforms in similar figures are determined as similar to each other, whereby the accuracy of determination on the similarity of the waveforms may be reduced.

SUMMARY

According to an aspect of an embodiment, a signal processor includes a memory and a processor coupled to the memory, wherein the processor executes a process. The processor executes a process including: detecting a signal; and calculating a correlation coefficient between waveforms of the signal included in a first window and a second window having a predetermined duration, the correlation coefficient being smaller when a difference between dispersion of the amplitude value in the first window and dispersion of the amplitude value in the second window becomes larger.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Preferred embodiments will be explained with reference to accompanying drawings. The embodiments herein are not intended to limit the scope of the invention. The embodiments can be combined appropriately as long as the various types of processing performed in the embodiments are not contradictory to each other.

[a] First Embodiment

Configuration of Pulse Wave Detection Apparatus

Figure 1:
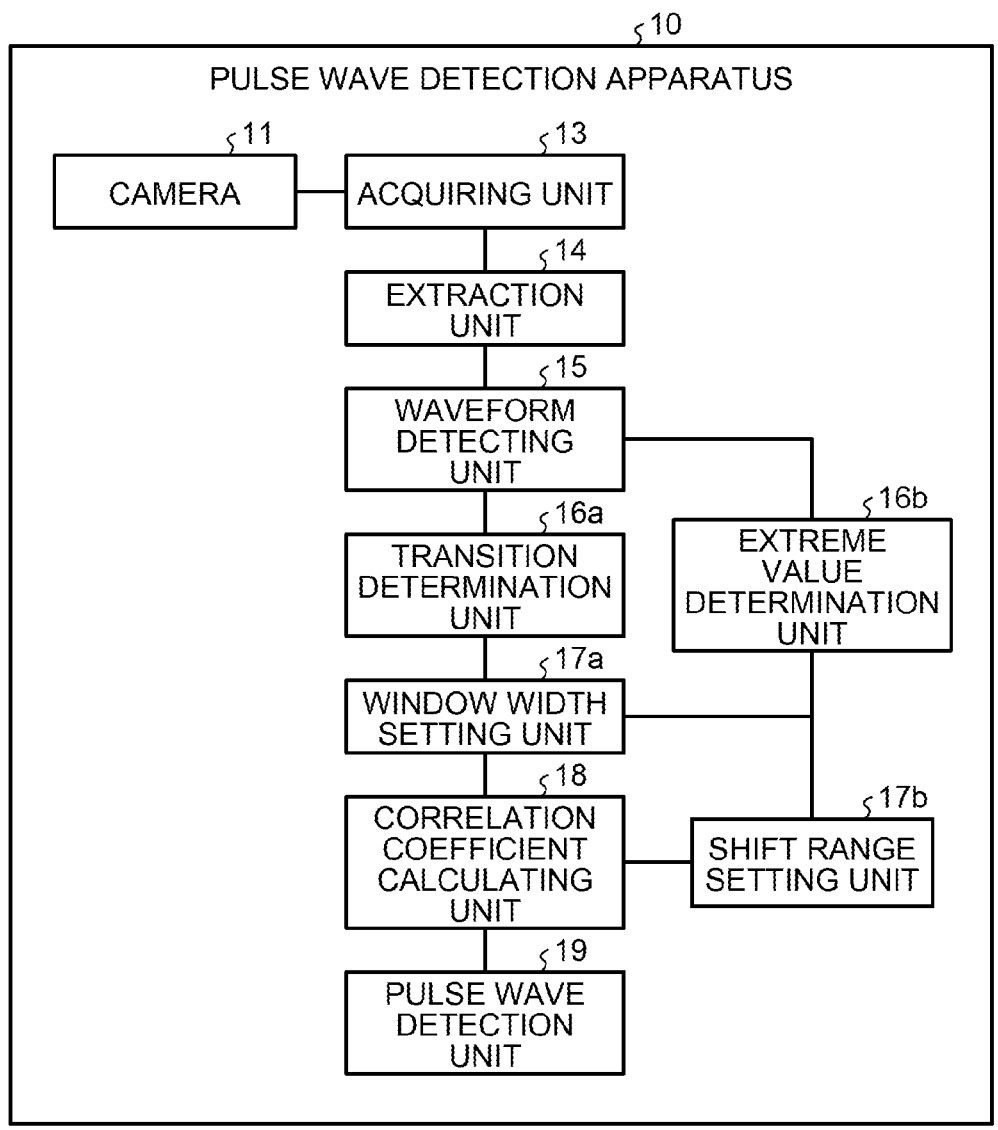
FIG. 1 is a block diagram illustrating the functional configuration of a pulse wave detection apparatus according to a first embodiment.

The following describes the functional configuration of a pulse wave detection apparatus according to a first embodiment. FIG. 1 is a block diagram illustrating the functional configuration of a pulse wave detection apparatus according to the first embodiment. A pulse wave detection apparatus 10 illustrated in FIG. 1 performs pulse wave detection processing. In the pulse wave detection processing, the fluctuation of the volume of the blood associated with a pulse wave, that is, heartbeats of a subject, is detected using an image in which the subject is captured under typical ambient light such as sunlight and room light, without contacting a measuring instrument with the living body of the subject.

As a part of the pulse wave detection, the pulse wave detection apparatus 10 determines whether a signal in the frequency band corresponding to the pulse wave detected from the image in which the living body of the subject is captured, is used for the pulse wave detection. This is determined by determining whether the waveform of the signal has a similarity to its waveform of the signal in the past, that is, the waveform of the signal has a periodicity. For the determination of the similarity, the pulse wave detection apparatus 10 calculates the correlation coefficient between a waveform of a signal included in a standard window having a predetermined duration and a waveform of a signal included in a comparison window that has been set backward in time from the standard window for comparison to the waveform in the standard window.

As described above, the pulse wave detection apparatus 10 according to the present embodiment performs signal processing in which the correlation coefficient is calculated when determining the similarity of the waveforms using the correlation coefficient. The larger the difference between the dispersion of the amplitude value in the standard window and the dispersion of the amplitude value in the comparison window, the smaller the value of the correlation coefficient becomes. In the pulse wave detection apparatus 10 according to the present embodiment, therefore, the correlation coefficient value is calculated to be low although the waveforms in the windows have a similarity relation to each other. With the pulse wave detection apparatus 10 according to the present embodiment, therefore, the accuracy of determination on the similarity of the waveforms can be improved.

As a mode of the embodiment, the pulse wave detection apparatus 10 can be implemented by installing a signal processing program in which the above-described signal processing is provided as package software or online software in a intended computer. For example, the above-described signal processing is installed not only in mobile communication terminals such as a smart phone, a mobile phone, and a personal handyphone system (PHS), but also in portable terminal devices such as a digital camera, a tablet terminal, and a slate terminal, which do not have a function for coupling to a mobile communication network. This enables the portable terminal device to function as the pulse wave detection apparatus 10. The pulse wave detection apparatus 10 is implemented as portable terminal devices here, however, the pulse wave detection apparatus 10 can be implemented by installing the signal processing program in a stand-alone type terminal device such as a personal computer.

As illustrated in FIG. 1, the pulse wave detection apparatus 10 includes a camera 11, an acquiring unit 13, an extraction unit 14, a waveform detecting unit 15, a transition determination unit 16a, an extreme value determination unit 16b, a window width setting unit 17a, a shift range setting unit 17b, a correlation coefficient calculating unit 18, and a pulse wave detection unit 19.

The pulse wave detection apparatus 10 may have various types of functions provided in already-known computers in addition to the functions illustrated in FIG. 1. For example, when the pulse wave detection apparatus 10 is implemented as a stand-alone type terminal device, the pulse wave detection apparatus 10 may have input and output devices such as a keyboard, a mouse, and a display. When the pulse wave detection apparatus 10 is implemented as a tablet terminal or a slate terminal, the pulse wave detection apparatus 10 may further include a touchpanel. Furthermore, when the pulse wave detection apparatus 10 is implemented as a mobile communication terminal, the pulse wave detection apparatus 10 may further include function units such as an antenna, a wireless communication unit coupled to a mobile communication network, and a global positioning system (GPS) receiver.

The camera 11 is an image capturing apparatus that has an image capturing element such as a charge coupled device (CCD) and a complementary metal oxide semiconductor (CMOS). For example, the camera 11 may have three or more types of light-receiving elements such as a red (R) light-receiving element, a green (G) light-receiving element, and a blue (B) light-receiving element. For example, the camera 11 may be implemented by coupling a digital camera or a Web camera to the pulse wave detection apparatus 10 through an external terminal. Alternatively, if a camera is mounted on the pulse wave detection apparatus 10 at the time of shipment, the camera can be applied to the camera 11. The pulse wave detection apparatus 10 having the camera 11 is described here, however, the pulse wave detection apparatus 10 does not always need to have the camera 11 when images can be obtained through a network or a storage device.

When an application program that performs the above-described pulse wave detection processing is pre-installed or installed in the pulse wave detection apparatus 10, capturing operations can be guided so that a user can capture such images of a subject that help detection of pulse waves using the camera 11. Hereinafter, the above-described application program may be referred to as an "application for pulse wave detection".

When the application for pulse wave detection is started up through a not-illustrated input device, the application for pulse wave detection starts up the camera 11. As a result, the camera 11 starts capturing images of a subject accommodated in a capture range of the camera 11. On this occasion, for capturing an image including the face of the subject, in the application for pulse wave detection, the image captured by the camera 11 can be displayed on a not-illustrated display device, with reference to the target position where the nose of the subject is captured. This enables the camera 11 to capture images accommodating the nose out of the parts of the face such as the eyes, the nose, and the mouth of the subject in the center of the capture range. In the application for pulse wave detection, the images in which the face of the subject is captured by the camera 11 are stored in the acquiring unit 13. Hereinafter, the image in which the face is captured may be referred to as a "face image".

The acquiring unit 13 is a processing unit that acquires images. As a mode of the embodiment, the acquiring unit 13 acquires a face image captured by the camera 11. As another mode of the embodiment, the acquiring unit 13 can acquire images from an auxiliary storage device that stores therein the face images such as a hard disk and an optical disk, or removal media such as a memory card and a universal serial bus (USB). As still another mode of the embodiment, the acquiring unit 13 can acquire the face image by receiving the face image from an external device through a network. In the description above, the acquiring unit 13 uses image data such as two-dimensional bitmap data or vector data obtained from the output from the image capturing element such as a CCD and a CMOS, thereby performing the processing. The acquiring unit 13 may, however, acquire a signal as it is output from a detector to perform the latter processing.

The extraction unit 14 is a processing unit that extracts a living body field out of the image acquired by the acquiring unit 13. As a mode of the embodiment, the extraction unit 14 extracts a living body field with reference to a predetermined face part out of the face image. For example, the extraction unit 14 performs image processing such as template matching on the face image, thereby detecting a specific face part, e.g., the nose out of the face parts such as the eyes, the ears, the nose, and the mouth of the subject. After that, the extraction unit 14 extracts the living body field included in a predetermined range with the nose of the subject as the center of the field. This extracts the image of the living body field including the nose of the subject and the center part of the face that is a part of the cheek surrounding the nose, as an image used for detecting pulse waves. The extraction unit 14 then outputs the image of the living body field extracted from the original image to the waveform detecting unit 15.

Figure 2:
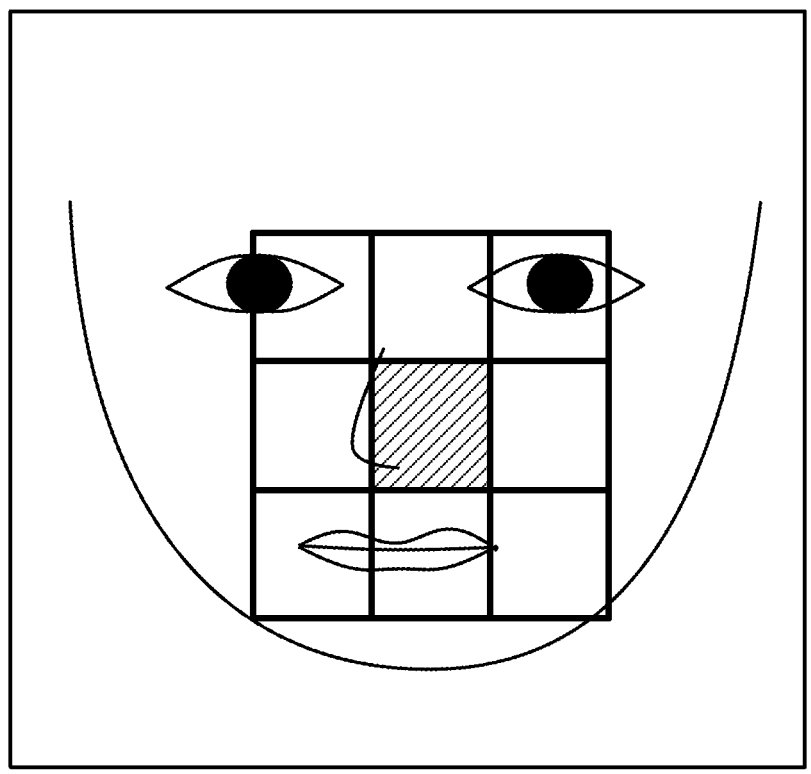
FIG. 2 is an exemplary diagram of a face image according to the first embodiment.

FIG. 2 is an exemplary diagram of a face image. FIG. 2 illustrates fields including a part or the whole of the eyes, the nose, or the mouth of the subject in the image, divided into nine blocks. The upper left block and the upper right block each include an eye of the subject out of the blocks illustrated in FIG. 2. When the images of the blocks are used for detection, blinks of the eyes may cause noise and therefore the accuracy of detection of the number of heartbeats may be reduced. The three blocks in the bottom line illustrated in FIG. 2 include the mouth of the subject. When the images of the blocks are used for detection, the movement of the mouth may cause noise and therefore the accuracy of detection of the number of heartbeats may be reduced. By contrast, the center block in the middle line illustrated in FIG. 2, that is, the block represented with hatched lines is separated from the blocks including the eyes and mouth. Therefore, the center block has less probability of including a component generating noise than other blocks, whereby a good detection result can be expected. For that reason, the extraction unit 14 extracts the image of the center block in the middle line illustrated in FIG. 2 as an image of the living body field from the original image.

After extracting the above-described image of the living body field, the extraction unit 14 performs a predetermined statistical processing on pixel values of the pixels included in the living body field. For example, the extraction unit 14 averages the pixel values of the pixels included in the living body field for each wavelength component. Alternatively, the median or the mode can be calculated rather than the average. Furthermore, arbitrary average processing such as weighted average processing and moving average processing can be performed, for example. As a result, the average of the pixel values of the pixels included in the living body field is calculated for each wavelength component as the representative value that represents the living body field.

The waveform detecting unit 15 is a processing unit that detects the waveform of the signal in which the components in the specific frequency band other than the possible pulse wave frequency band where the pulse wave may appear in each wavelength component are offset with each other, from the signals of the representative value for each wavelength component of the pixels included in the targeted living body field for detection of pulse waves.

As a mode of the embodiment, the waveform detecting unit 15 detects waveforms using time-series data of the representative values of two wavelength components, an R component and a G component, which have different light absorption characteristics from each other out of the three wavelength components included in an image, that is, a red (R) component, a green (G) component, and a blue (B) component.

This will be described in detail as follows. Capillaries flow on the surface of the human face. When the blood flow flown through blood vessels changes due to heartbeats, the amount of light absorbed by the blood flow also changes according to heartbeats, whereby the brightness obtained by the reflection from the face also changes in associated with heartbeats. Although the amount of change of the brightness is small, when the average of the brightness in the entire field of the face is calculated, a pulse wave component is included in the time-series data of the brightness. However, the brightness also changes due to the body movement in addition to the pulse wave, which generates a noise component of the pulse wave detection, that is, body movement artifacts. A pulse wave is detected using two or more wavelengths having different light absorption characteristics of the blood, that is, a G component having a high light absorption characteristic (approximately 525 nm) and an R component having a low light absorption characteristic (approximately 700 nm). Heartbeats have a frequency of 0.5 to 4 Hz ranging from 30 to 240 beats per minute (bpm) converted into the frequency per minute. The components outside of the range are considered to be noise components. Assuming that noise has no or minimal wavelength characteristics, if any, the components outside of the range from 0.5 to 4 Hz are considered to be equal to each other between the G signal and the R signal. Actually, however, the components outside of the range from 0.5 to 4 Hz are different from each other between the G signal and the R signal due to the sensitivity difference of the camera. Correcting the sensitivity difference of the components outside of the range from 0.5 to 4 Hz and subtracting the R component from the G component, therefore, eliminates the noise components and extracts only the pulse wave components.

For example, the G component and the R component are represented by the following Expression (1) and Expression (2). "Gs" in the following Expression (1) means a pulse wave component of the G signal, "Gn" means a noise component of the G signal. "Rs" in the following Expression (2) means a pulse wave component of the R signal, "Rn" means a noise component of the R signal. The noise components have the sensitivity difference between the G component and the R component, therefore, the correction coefficient k for the sensitivity difference is represented by the following Expression (3).

$$Ga = Gs + Gn \quad (1)$$

$$Ra = Rs + Rn \quad (2)$$

$$k = Gn/Rn \quad (3)$$

By correcting the sensitivity difference and subtracting the R component from the G component, a pulse wave component S is obtained as the following Expression (4). By changing Expression (4) into an expression represented with Gs, Gn, Rs, and Rn using the above-described Expression (1) and Expression (2), the following Expression (5) is obtained. By organizing the expression using the above-described Expression (3) to eliminate k, the following Expression (6) is derived.

$$S = Ga - kRa \quad (4)$$

$$S = Gs + Gn - k(Rs + Rn) \quad (5)$$

$$S = Gs - (Gn/Rn)Rs \quad (6)$$

The G signal and the R signal have different light absorption characteristics from each other, while Gs>(Gn/Rn)Rs. Therefore, with the above-described Expression (6), the pulse wave component S in which the noise is eliminated can be calculated.

Figure 3:
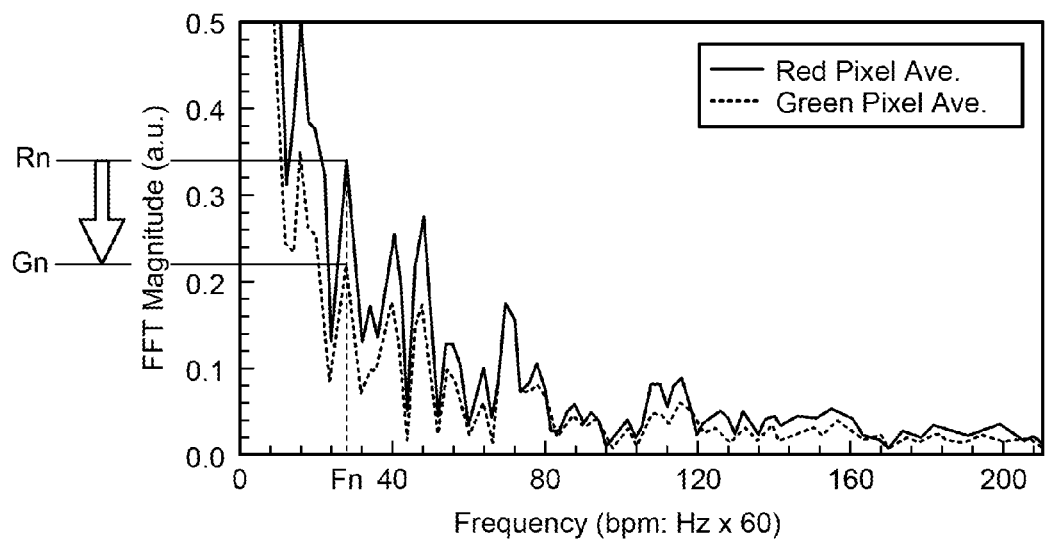
FIG. 3 is an exemplary diagram of a spectrum of a G signal and an R signal according to the first embodiment.

FIG. 3 is an exemplary diagram of the spectra of the G signal and the R signal. The vertical axis of the graph illustrated in FIG. 3 represents the signal intensity and the horizontal axis of the graph represents the frequency (bpm). As illustrated in FIG. 3, the G component and the R component have different sensitivities of the image capturing elements from each other, therefore, the signal intensities of the G component and the R component are different from each other. In the R component and the G component, however, noise still appears outside of the range from 30 to 240 bpm, especially in the specific frequency band ranging from not less than 3 to less than 20 bpm. Accordingly, as illustrated in FIG. 3, the signal intensity corresponding to a specified frequency Fn included in the specific frequency band ranging from not less than 3 to less than 20 bpm is extracted as Gn and Rn. The Gn and Rn derive the correction coefficient k for the sensitivity difference.

Figure 4:
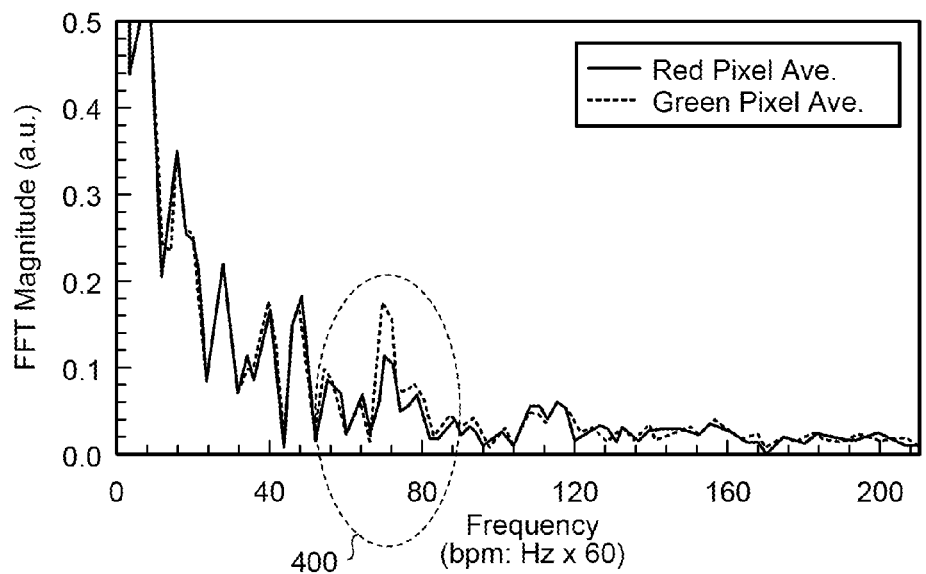
FIG. 4 is an exemplary diagram of a spectrum of a signal including a G component and a signal including an R component multiplied by a correction coefficient k according to the first embodiment.

FIG. 4 is an exemplary diagram of a spectrum of a signal including the G component and the R component multiplied by the correction coefficient k. For convenience of description, the result of multiplying the R component by the absolute value of the corrected coefficient is illustrated in the example in FIG. 4. Also in FIG. 4, the vertical axis of the graph illustrated represents the signal intensity and the horizontal axis of the graph represents the frequency (bpm). As illustrated in FIG. 4, in the spectrum of a signal including the G component and a signal including the R component, when the R component is multiplied by the correction coefficient k, the sensitivities between the G component and the R component are equivalent to each other. In particular, the signal intensities of the spectra seem to be almost the same in the specific frequency band for the most part. By contrast, in a surrounding field 400 of the frequency actually including pulse waves, the signal intensities of the spectra are not equivalent between the G component and the R component.

Figure 5:
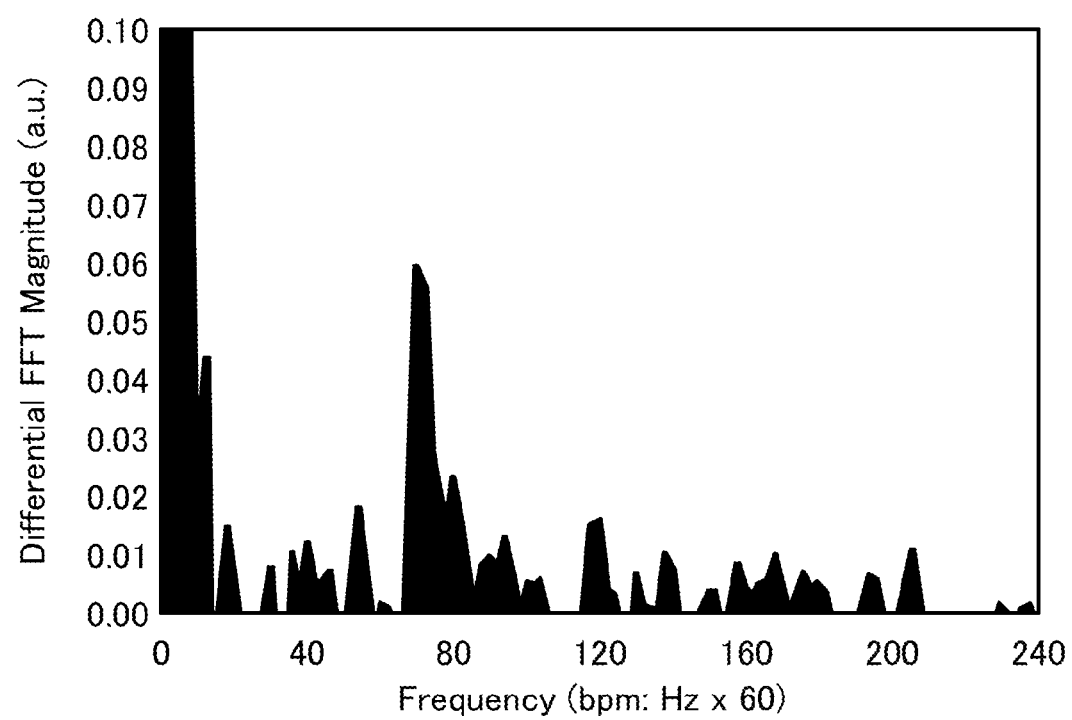
FIG. 5 is an exemplary diagram of a spectrum after computation according to the first embodiment.

FIG. 5 is an exemplary diagram of a spectrum after computation. From the viewpoint of increasing the visibility of the frequency band in which a pulse wave appears, the scale of the signal intensity serving as the vertical axis is illustrated larger in the graph illustrated in FIG. 5 than other graphs illustrated in other diagrams. As illustrated in FIG. 5, when the spectrum of the R signal after being multiplied by the correction coefficient k is subtracted from the spectrum of the G signal, the noise component is reduced while the intensity of the signal component at which a pulse wave appears due to the difference of the light absorption characteristics between the G component and the R component is maintained as long as possible. As described above, the pulse waveform from which only the noise component has been eliminated can be detected.

Figure 6:
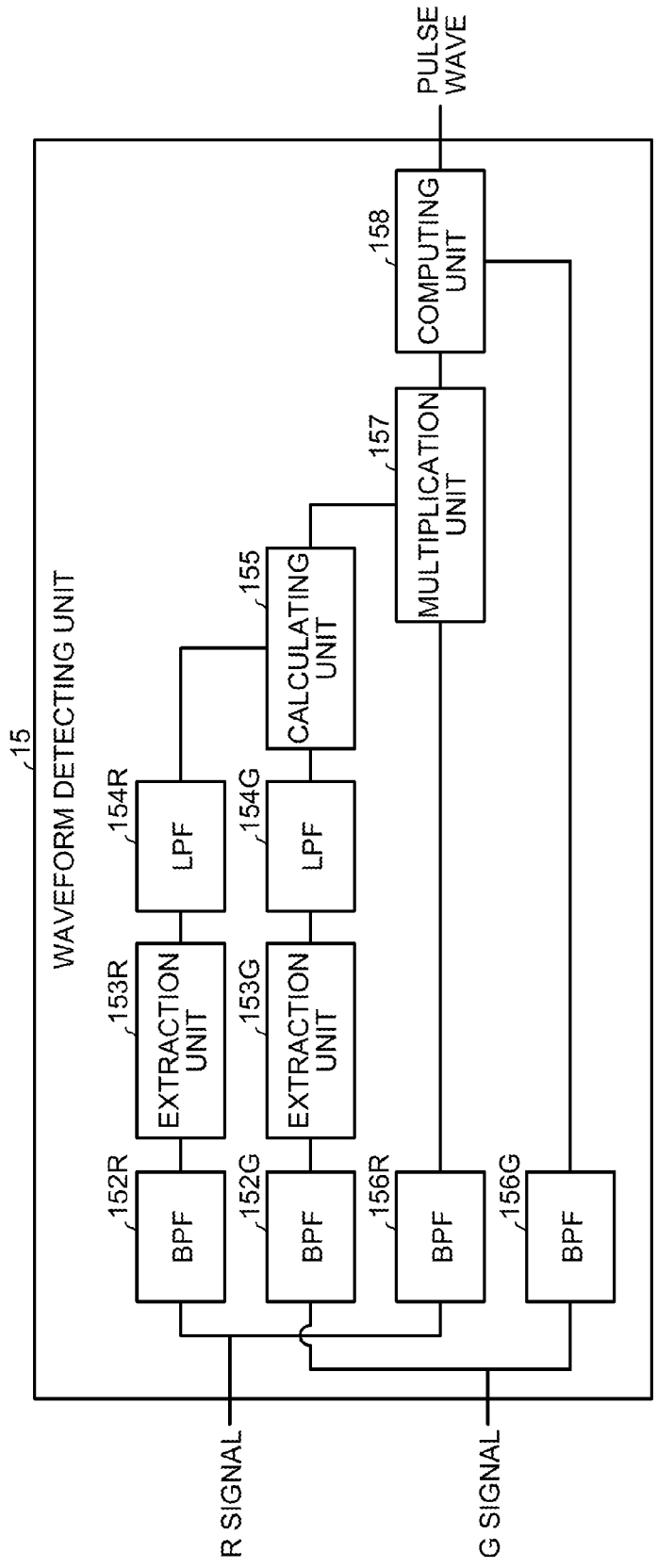
FIG. 6 is a block diagram illustrating the functional configuration of a waveform detecting unit according to the first embodiment.

The functional configuration of the waveform detecting unit 15 is described in more detail. FIG. 6 is a block diagram illustrating the functional configuration of the waveform detecting unit 15. As illustrated in FIG. 6, the waveform detecting unit 15 includes band-pass filters (BPF) 152R and 152G, extraction units 153R and 153G, low-pass filters (LPF) 154R and 154G, a calculating unit 155, BPFs 156R and 156G, a multiplication unit 157, and a computing unit 158. Pulse waves are detected in the frequency space in the examples illustrated in FIGS. 3 to 5. By contrast, FIG. 6 illustrates the functional configuration when the noise component is cancelled in the time-series space for detecting the pulse wave, from the viewpoint of reducing the time for converting into the frequency component.

For example, from the extraction unit 14 to the waveform detecting unit 15, the time-series data of the R signal is input in which the representative value of the pixel values of the pixels in the R component included in the living body field is determined as a signal value. The time-series data of the G signal is also input in which the representative value of the pixel values in the pixels of the G component included in the living body field is determined as a signal value. Among them, the R signal in the living body field is input to the BPF 152R and the BPF 156R in the waveform detecting unit 15, and the G signal of the living body field is input to the BPF 152G and the BPF 156G in the waveform detecting unit 15.

The BPF 152R, the BPF 152G, the BPF 156R, and the BPF 156G are all band path filters that allow only the signal components in a predetermined frequency band to pass through and eliminate the signal components in other frequency bands. The BPF 152R, the BPF 152G, the BPF 156R, and the BPF 156G may be implemented by hardware or software.

The following describes the difference of the frequency bands allowed to pass through by the BPFs. The BPF 152R and the BPF 152G allow the signal component in the specific frequency band in which the appearance of a noise component is more obvious than in other frequency bands to pass through.

The specific frequency band can be determined by comparing a frequency band to possible frequency bands in which a pulse wave may appear. Examples of the possible frequency band in which a pulse wave may appear include the frequency band ranging from 0.5 to 4 Hz, that is, ranging from 30 to 240 beats per minute (bpm) when converted into the frequency per minute. Accordingly, the frequency band less than 0.5 Hz and the frequency band more than 4 Hz, for example, can be adopted as the specific frequency band because they are not measured as pulse waves. The specific frequency band may partly overlap with a frequency band in which a pulse wave may appear. For example, the specific frequency band may overlap with a frequency band in which a pulse wave may appear in the section ranging from 0.7 to 1 Hz where the frequency is seldom measured as a pulse wave and the frequency band less than 1 Hz and the frequency band not less than 4 Hz may be adopted as the specific frequency band. The specific frequency band may be determined so as to be limited to the frequency band having an outer edge of the frequency band less than 1 Hz and an outer edge of the frequency band not less than 4 Hz, in which the appearance of noise is more obvious. For example, the appearance of noise is more obvious in a low frequency band lower than the frequency band in which a pulse wave appears, than a high frequency band higher than the frequency band in which a pulse wave appears. For this reason, the specific frequency band may be limited to the frequency band less than 1 Hz. Alternatively, the frequency band may be limited to the specific frequency band ranging from not less than 3 to less than 60 bpm because large differences in sensitivity of image capturing elements for each component are included in the vicinity of a direct current component whose space frequency is zero. Furthermore, the specific frequency band can be limited to the frequency band ranging from not less than 3 to less than 20 bpm where noise is likely to appear due to human body movements such as blinks of the eyes or swings of the body, or blinks of environmental light.

For example, in the following description, it is assumed that the BPF 152R and the BPF 152G allow the signal component in the frequency band ranging from 0.05 to 0.3 Hz to pass through as the specific frequency band. The band path filter is used for extracting the signal component in the specific frequency band in this example. A low path filter may be used, however, when extracting the signal component in the frequency band less than a certain frequency, for example.

By contrast, the BPF 156R and the BPF 156G allow the signal component in the frequency band ranging from 1 to 4 Hz in which a pulse wave may appear, for example. Hereinafter, the frequency band in which a pulse wave may appear may be referred to as a "pulse wave frequency band".

The extraction unit 153R extracts the absolute intensity value of the signal component in the specific frequency band of the R signal. For example, the extraction unit 153R performs multiplication processing in which the signal component in the specific frequency band of the R signal is raised, thereby extracting the absolute intensity value of the signal component in the specific frequency band. The extraction unit 153G extracts the absolute intensity value of the signal component in the specific frequency band of the G signal. For example, the extraction unit 153G performs multiplication processing in which the signal component in the specific frequency band of the G signal is raised, thereby extracting the absolute intensity value of the signal component in the specific frequency band.

The LPF 154R and the LPF 154G are low path filters that perform smoothing processing for response to the time change on the time-series data of the absolute intensity value in the specific frequency band. The only difference between the LPF 154R and the LPF 154G is that the R signal is input to the LPF 154R and the G signal is input to the LPF 154G. The smoothing processing calculates the absolute intensities in the specific frequency bands R'n and G'n.

The calculating unit 155 performs the division "G'n/R'n", that is, the absolute intensity G'n in the specific frequency band of the G signal output by the LPF 154G is divided by the absolute intensity R'n in the specific frequency band of the R signal output by the LPF 154R. As a result, the correction coefficient k for the sensitivity difference is calculated.

The multiplication unit 157 multiplies the signal component in the specific frequency band of the R signal output by the BPF 156R by the correction coefficient k calculated by the calculating unit 155.

The computing unit 158 performs computation "k*Rs−Gs", that is, the signal component in the specific frequency band of the G signal output by the BPF 156G is subtracted from the signal component in the specific frequency band of the R signal multiplied by the correction coefficient k by the multiplication unit 157. The time-series data of the signal obtained from the computation corresponds to the waveform of a pulse wave.

As described above, the pulse waveform detected in the living body field of an image is output to the transition determination unit 16a and the extreme value determination unit 16b. Hereinafter, the ith time in the pulse waveform may be referred to as "t(i)", and the amplitude value in the pulse waveform may be referred to as "v(i)". In addition, the latest index in the pulse waveform may be referred to as "I". The interval of the times t(i) when the amplitude value in the pulse waveform is obtained, that is, a frame rate is constant and represented with "δ".

With referring to FIG. 1 again, the transition determination unit 16a is a processing unit that determines whether the positive/negative of the amplitude value of the signal detected by the waveform detecting unit 15 transitions. As a mode of the embodiment, the transition determination unit 16a determines whether the positive/negative of the amplitude value of the pulse waveform transitions every time the waveform detecting unit 15 outputs the amplitude value of a pulse waveform. If the following Expression (7) or Expression (8) is satisfied, the transition determination unit 16a determines that the positive/negative of the amplitude value v(i) transitions. As described above, the transition determination unit 16a sequentially records the time T(j)=t(I) when the positive/negative of the amplitude value transitions in a not-illustrated internal memory, for example. The above-described "j" means an ordinal number of the transition point. The index of the latest transition point is represented with "J".

$$v(i-1)<0 \text{ and } v(i)\geq 0 \quad (7)$$

$$v(i-1)\geq 0 \text{ and } v(i)<0 \quad (8)$$

The extreme value determination unit 16b is a processing unit that determines whether the amplitude value of the signal detected by the waveform detecting unit 15 is an extreme value. As a mode of the embodiment, the extreme value determination unit 16b determines whether the amplitude value of a pulse waveform including the index preceded by one from the index at which the amplitude value of the pulse waveform is output is the maximum value every time the waveform detecting unit 15 outputs the amplitude value of a pulse waveform. If the following Expression (9) is satisfied, the extreme value determination unit 16b determines that the amplitude value v(i−1) is the maximum value. As described above, the extreme value determination unit 16b sequentially records the time M(k)=t(I−1) that is a time when the amplitude value is the maximum value in the internal memory. The above-described "k" means an ordinal of a local maximum point. In addition, the index of the latest local maximum point may be referred to as "K".

$$v(i-2)\leq v(i-1) \text{ and } v(i-1)>v(i) \quad (9)$$

The window width setting unit 17a is a processing unit that sets the duration of a standard window. The standard window means the window a waveform of which is determined whether to be used for detecting a pulse wave out of the two windows. In the standard window, the section backward in time by a predetermined duration from the latest time t(I) is set, for example. Hereinafter, the duration of the window may be referred to as a "width of window". The width of window needs not to be set every time the amplitude value of a pulse waveform is obtained. The width of window may be set only when a predetermined condition for setting the standard window is satisfied. For example, the condition for setting the standard window is that setting of the width of window may be started triggered by elapsing of a given parameter, elapsing of a second, for example, from the prior setting of the standard window. For another example, setting of the width of window may be started when the latest index I is a transition point.

As a mode of the embodiment, the window width setting unit 17a may set a given parameter, e.g., three seconds to a width of window U. The window width setting unit 17a may set an arbitrary parameter to the width of window U other than the above-described three seconds, as long as it has the duration not less than 42 bpm, which is the minimum human pulse rate.

As another mode of the embodiment, the window width setting unit 17a sets the length of the section backward in time until the number of transition points at which the transition determination unit 16a determines that the positive/negative of the amplitude value transitions becomes equal to the number corresponding to the integral multiple of the period of the pulse wave, as the duration of the standard window. For example, the window width setting unit 17a calculates the difference between the time T(J) of the latest transition point and the time T(J−2*n) preceded by two periods in the pulse wave, for the number of the transition point corresponding to the period of the pulse wave "n", thereby determining the width of window U.

$$U=T(J)-T(J-2*n) \quad (10)$$

In the setting of the width of window using the transition point, the periodicity in which the positive and negative values are repeated around 0 in synchronization with the pulse wave is utilized, in the state in which the pulse waveform has a pulse wave frequency band, that is, a signal component of 42 to 240 bpm, which is a stable measurement condition of the pulse wave. Accordingly, under the condition in which the measurement condition of the pulse wave is stable, the standard window may include the number of the transition points corresponding to the number of the integral multiple of, in this example, twice the number "n" of the transition point corresponding to one period of the pulse wave.

Figure 7:
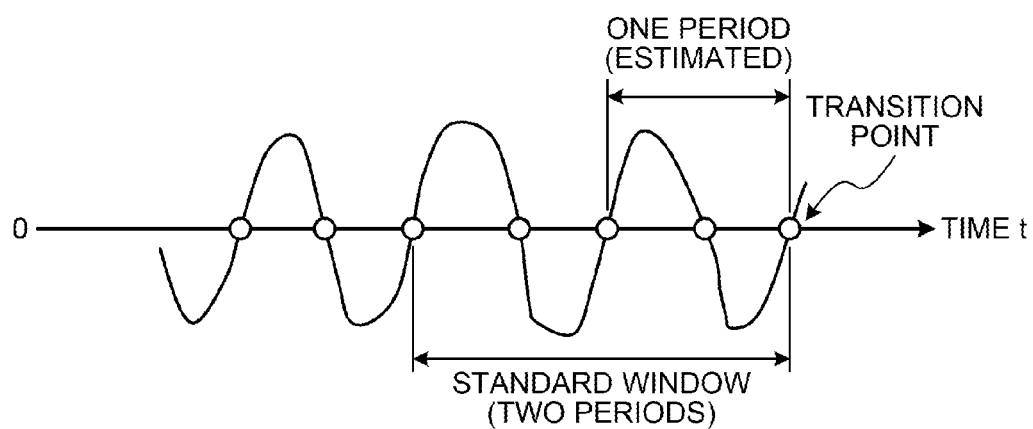
FIG. 7 is an exemplary diagram of a method for setting the width of window according to the first embodiment.

FIG. 7 is an exemplary diagram of a method for setting the width of window. The vertical axis of the graph illustrated in FIG. 7 represents the amplitude and the horizontal axis represents the time. As illustrated in FIG. 7, to trace back the pulse wave by one period, two transition points are traced back except for the latest transition point. To trace back the pulse wave by two periods, therefore, four (=2*n) transition points are traced back. As described above, when setting the width of window U using Expression (10), the integral multiple of the period approximating the period of a pulse wave actually measured may be set to the width of window. The width of window having a shorter time than the minimum pulse rate, 42 bpm, for example, may be set, whereby the calculation amount in the correlation coefficient calculating unit 18 described later can be reduced.

With referring to FIG. 1 again, the shift range setting unit 17b is a processing unit that sets the range for shifting the comparison window. Hereinafter, the range for shifting the comparison window may be referred to as a "shift range". The shift range setting unit 17b here does not always set the shift range after the window width setting unit 17a sets the width of the standard window. Specifically, the shift range setting unit 17b performs setting of the shift range when the number of the local maximum points included in the standard window the duration of which has been set by the window width setting unit 17a, out of the local maximum points determined as the local maximum by the extreme value determination unit 16b is equal to the number corresponding to the period of the pulse wave.

The following describes this in detail. The shift range setting unit 17b firstly calculates the number of the local maximum points included in the standard window. For example, the shift range setting unit 17b counts an integer k that satisfies the condition of the following Expression (11). The shift range setting unit 17b then determines whether the number of the local maximum points included in the standard window M(k) exceeds the number of the local maximum points corresponding to one period of the pulse wave. On this occasion, if more local maximum points exist in the standard window than the number "n" of the local maximum points corresponding to one period of the pulse wave, measurement condition may be considered to be unstable. As a result, the shift range setting unit 17b does not set the shift range. As described above, the number of the local maximum points is used for a starting condition of setting the shift range because a higher number of local maximum points exceeding the ideal number of local maximum points is considered to be a result of change in the measurement condition. The ideal number of local maximum points per period in a pulse waveform is one.

$$T(J)-U \leq M(k) \leq T(J) \quad (11)$$

Figure 8:
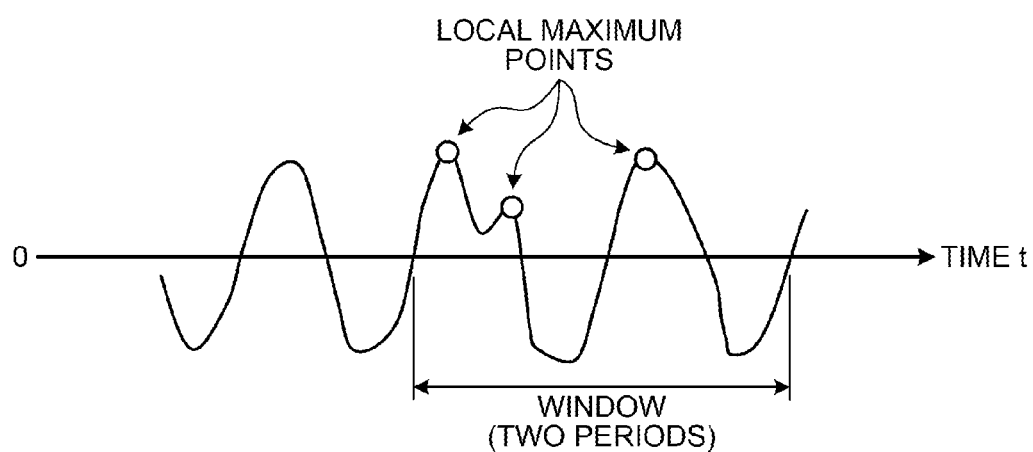
FIG. 8 is an exemplary diagram of local maximum points included in a pulse waveform according to the first embodiment.

FIG. 8 is an exemplary diagram of local maximum points included in the pulse waveform. The vertical axis of the graph illustrated in FIG. 8 represents the amplitude and the horizontal axis represents the time. As illustrated in FIG. 8, the standard window having the width of window of two periods of the pulse wave includes three local maximum points. Under the measurement state in which noise can be ignored, only one local maximum point appears per one period of the pulse wave. Accordingly, noise is considered to be superimposed in the signal in the standard window illustrated in FIG. 8, to the extent that the noise interferes with peak detection. The computing after that may be cancelled. By cancelling the setting of the shift range and the calculation of the correlation coefficient due to the pulse waveform in which noise is superimposed, the calculation amount can be reduced.

As described above, the shift range setting unit 17b starts setting of the shift range when the number of the local maximum points included in the standard window M(k) is less than the number "n" of the local maximum points corresponding to one period of the pulse wave.

As a mode of the embodiment, the shift range setting unit 17b may set the shift range with reference to the possible range of generally known number of the human pulse rate, e.g., 42 to 240 bpm. For example, the shift range setting unit 17b may set the shift range w (sec.) from the range represented by the following Expression (12). Rmin and Rmax in the following Expression (12) is represented by the following Expression (13) and Expression (14). The shift range as described above is set because the shift range in which the correlation coefficient obtained in the correlation coefficient calculating unit becomes the maximum corresponding to the time of a pulse if the pulse waveform originates mainly from the pulse wave of the subject.

$$R\min \leq w \leq R\max \quad (12)$$

$$R\min=60/240 \quad (13)$$

$$R\max=60/42 \quad (14)$$

As another mode of the embodiment, the shift range setting unit 17b may estimate the period of the pulse based on the interval of the transition points. The difference between the time of the latest transition point and the time of the transition point proceeded by the number of m*2 for a given parameter m is about m times of the pulse wave. Therefore, the time for one period in the present pulse wave of the subject is estimated to be "(T(J)−T(J−2*m))/m (sec.)". The shift range w (sec.) is therefore set to the range represented by the following Expressions (15) to (17) for a given parameter γ larger than 0 and smaller than 1.

$$R\min=\max(60/240,\gamma(T(J)-T(J-2*m))/m) \quad (15)$$

$$R\max=\min(60/42,(T(J)-T(J-2*m))/m/\gamma) \quad (16)$$

$$R\min \leq w \leq R\max \quad (17)$$

As still another mode of the embodiment, the shift range setting unit 17b obtains the difference between the time of the latest transition point and the time of the transition point preceded by the number of n*2 where n=m in the window width setting unit 17a. When the obtained value is determined as the width of window U, the shift range w (sec.) can be set to the range represented by the following Expressions (18) to (20).

$$Rmin = \max(60/240, \gamma U/n) \qquad (18)$$

$$Rmax = \min(60/42, U/n/\gamma) \qquad (19)$$

$$Rmin \leq w \leq Rmax \qquad (20)$$

Figure 9:
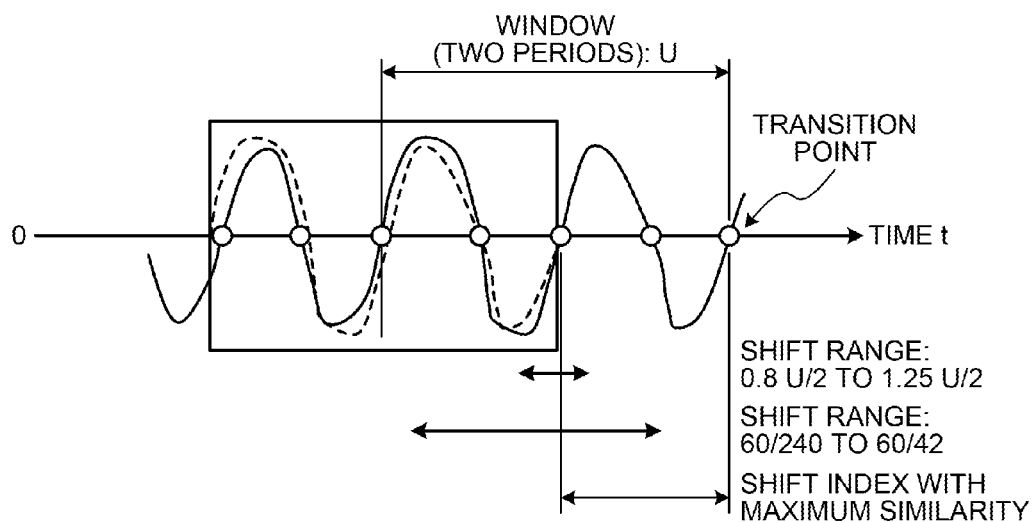
FIG. 9 is an exemplary diagram of a setting of a shift range according to the first embodiment.

FIG. 9 is an exemplary diagram of setting of the shift range. The shift range when m=n=2, γ=0.8 is illustrated in FIG. 9. The vertical axis of the graph illustrated in FIG. 9 represents the amplitude and the horizontal axis represents the time. In FIG. 9, the pulse waveform is represented with a solid line, and the pulse waveform in the standard window is represented with a dashed line superimposed in the comparison window. As illustrated in FIG. 9, the range that has been set based on the interval of the transition points, that is, 0.8 U/2 to 1.25 U/2 is narrower than the range that has been set so as to include the possible maximum and minimum numbers of the human pulse rate, that is, 60/150 to 60/42. As described above, by estimating the period of the pulse based on the transition points, the shift range becomes small. This prevents an erroneous detection of unstable pulse waves by removing a shift range significantly apart from the number of pulse rates of the subject in advance and reduces the calculation amount in the correlation coefficient calculating unit. The width of window U is used in the description above, however, the interval of the local maximum points can be used.

In all examples described above, when Rmax<Rmin, the shift range does not exist. On this occasion, the later-described processing by the correlation coefficient calculating unit 18 is not performed.

With reference to FIG. 1 again, the correlation coefficient calculating unit 18 is a processing unit that calculates the correlation coefficient between the pulse waveform in the standard window and the pulse waveform in the comparison window.

The following describes this in detail. The correlation coefficient calculating unit 18 firstly obtains a candidate of a shift index z, {z}. The {z} means all integers where zδ is included in [Rmin, Rmax] for the shift range [Rmin, Rmax] calculated by the shift range setting unit 17b. The minimum value of {z} is referred to as Zmin, and the maximum value of {z} is referred to as Zmax. The number of indexes of the pulse waveform included in the standard window is determined as X. As in the above-described example, when the standard window is set based on the transition point, the X becomes "T(J)−T(J−2*n)+1". The values of the pulse waveform included in the standard window are lined up in the order of time as x (1), x (2), . . . , x (X) and written as follows.

$$x(1) = v(I - X - 1)$$
$$x(2) = v(I - X - 2)$$
$$\ldots$$
$$x(X) = v(I)$$

In the same manner, the values of the pulse waveform included in the comparison window shifted by z from the standard window are lined up in the order of time as y (1), y (2), . . . , y (X) and written as follows.

$$y(z, 1) = v(I - X - 1 - z)$$
$$y(z, 2) = v(I - X - 2 - z)$$
$$\ldots$$
$$y(z, X) = v(I - z)$$

As described above, the correlation coefficient calculating unit 18 calculates the candidate of the shift index z, {z}, and then calculates the correlation coefficient between the pulse waveform in the standard window and the pulse waveform in the comparison window shifted by z from the standard window, for each of z in {z}.

As a mode of the embodiment, the correlation coefficient calculating unit 18 calculates the correlation coefficient S(z) while incrementing the shift index z one by one from Zmin to Zmax. The correlation coefficient is an index indicating that the larger the value, the more similar are the pulse waveform in the standard window and the pulse waveform in the comparison window shifted by z from the standard window. For example, the correlation coefficient can be calculated according to the following Expression (21). After the correlation coefficients are calculated for all of the candidates for the shift index {z} as described above, the shift index where S(z) becomes the maximum is determined as Z. The average of x(1), x(2), . . . , x(X) and the average of y(z, 1), y(z, 2) . . . , y(z, X) may be substituted with 0 because of the characteristic of the pulse waveform in which the positive and negative values are repeated around 0.

$$S(z) = \frac{\sum_{i=1}^{x}(x(i) - \overline{x})(y(z, i) - \overline{y(z)})}{\sqrt{\sum_{i=1}^{x}(x(i) - \overline{x})^2} \sqrt{\sum_{i=1}^{x}(y(z, i) - \overline{y(z)})^2}} \qquad (21)$$

$\overline{x}$ is the average of $x(1), \ldots, x(X)$.

$\overline{y(z)}$ is the average of $y(z, 1) \ldots, y(z, X)$.

Figure 10:
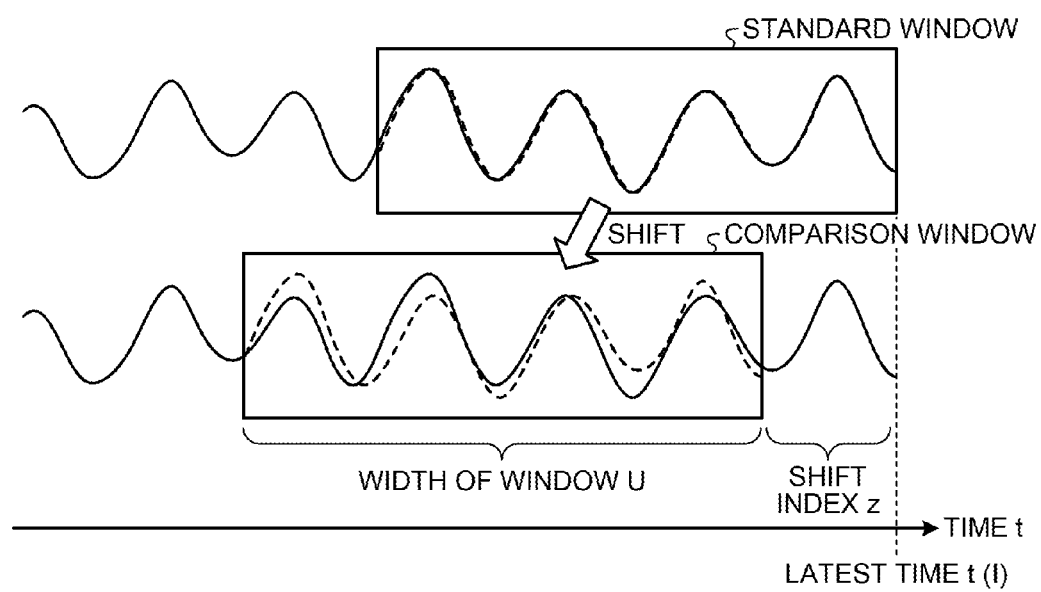
FIG. 10 is an exemplary diagram of waveforms in a standard window and a comparison window according to the first embodiment.

FIG. 10 is an exemplary diagram of waveforms in the standard window and the comparison window. The vertical axis of the graph illustrated in FIG. 10 represents the amplitude and the horizontal axis represents the time. In FIG. 10, the pulse waveform is represented with a solid line, and the pulse waveform in the standard window is represented with a dashed line superimposed in the comparison window. As illustrated in FIG. 10, the pulse waveform in the standard window has a quite similar shape to that of the pulse waveform in the comparison window shifted by z from the standard window. As described above, when the standard window and the comparison window have waveforms in similar shape to each other, the calculated correlation coefficient becomes higher.

Subsequently, the correlation coefficient calculating unit 18 compares S(Z) and a predetermined threshold β. If S(Z) is smaller than β, the correlation coefficient calculating unit 18 determines that no comparison window similar enough to the standard window is found and thus does not allow the pulse wave detection unit 19 to detect the pulse wave.

Appropriate values can be specified for the threshold β. For example, the value of approximately 0.6 to 0.8 is specified for the threshold β because it is apparent that the maximum value is 1 for the correlation coefficient. This improves the accuracy of determination on the periodicity of the waveform.

When calculating the correlation coefficient by dividing the covariance by the standard deviation as the above-described Expression (21), and if the pulse waveform fluctuates larger in the standard window, then the calculated correlation coefficient of waveforms has a similar shape, that is, homothetic waveforms becomes higher although the respective amplitude values in the standard window and the comparison window significantly differs from each other.

Figure 11:
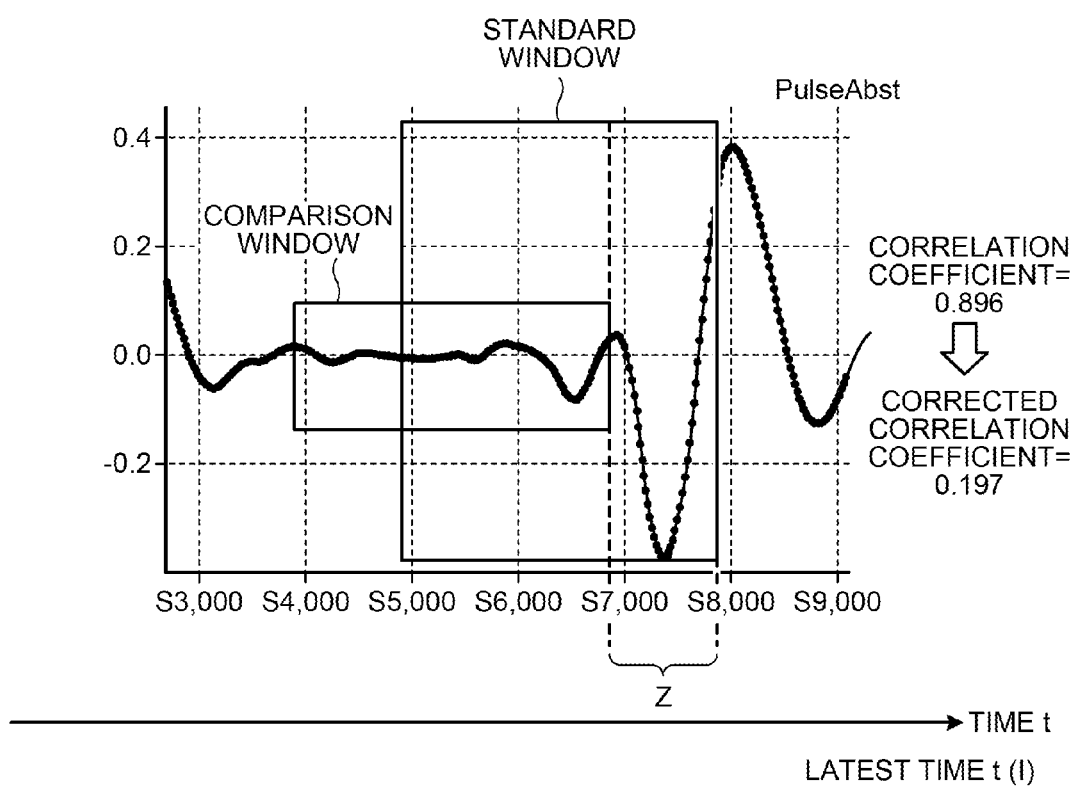
FIG. 11 is an exemplary diagram of waveforms in the standard window and the comparison window according to the first embodiment.

FIG. 11 is an exemplary diagram of waveforms in the standard window and the comparison window. The vertical axis of the graph illustrated in FIG. 11 represents the amplitude and the horizontal axis represents the time. As illustrated in FIG. 11, the amplitude of the pulse waveform may become larger in the standard window because of change of the measurement condition. As described above, if the amplitude of the pulse waveform may become larger in the latter end of the standard window, the area where the amplitude of the pulse waveform is larger is excluded in the window where the time is shifted by Z from the standard window. On this occasion, when the above-described Expression (21) is used for the calculation of the correlation coefficient, the correlation coefficient tends to become quite large. This is caused by the separate normalization for the respective windows in calculation of the correlation coefficient. The respective areas where the amplitude of the pulse waveform is larger on the right side of the windows are considered to almost match to each other after the normalization. On this occasion, other areas in the windows (on the left side of the windows) are seldom influenced by the correlation coefficient value. For example, in the example illustrated in FIG. 11, the correlation coefficient value becomes 0.896. When the above-described Expression (21) is used for the calculation of the correlation coefficient, the correlation coefficient may become large even when the measurement condition is unstable. This may cause use of unstable pulse waveforms for detection.

For that reason, as illustrated in the following Expression (22), the correlation coefficient calculating unit 18 calculates the corrected correlation coefficient by selecting the larger dispersion out of the dispersion in the standard window and the dispersion in the comparison window and using the selected dispersion. The corrected correlation coefficient value becomes equal to the correlation coefficient value only when the dispersion in the pulse waveforms in both windows is equal to each other. The larger the difference of the dispersion in the pulse waveforms in both windows, the smaller the value calculated relatively than the correlation coefficient (where the value is positive). As illustrated in FIG. 11, therefore, when the dispersion in the pulse waveforms in both windows are different from each other, the corrected correlation coefficient value becomes small and thus the pulse waveform can no longer be output. For example, In the example illustrated in FIG. 11, the correlation coefficient value is 0.896 while the corrected correlation coefficient value is 0.197, that is, a quarter of the correlation coefficient value, which is smaller than the threshold β. The calculation of the corrected correlation coefficient as described above can suppress the issue that when the standard window and the comparison window have waveforms in similar shape to each other, the calculated correlation coefficient becomes higher regardless of the large difference between the amplitude values in both windows. Again, the value of approximately 0.6 to 0.8 may be usually specified for the threshold β because it is apparent that the maximum value is 1 for the corrected correlation coefficient.

$$S(z) = \frac{\sum_{i=1}^{x} (x(i) - \overline{x})(y(z, i) - \overline{y(z)})}{\max\left(\sum_{i=1}^{x} (x(i) - \overline{x})^2, \sum_{i=1}^{x} (y(z, i) - \overline{y(z)})^2\right)} \qquad (22)$$

With referring to FIG. 1 again, the pulse wave detection unit 19 is a processing unit that detects a pulse wave from the waveform output by the correlation coefficient calculating unit 18. As a mode of the embodiment, the pulse wave detection unit 19 detects stable pulse waves such as the pulse rate and the pulse waveform of a subject and outputs them. That is, it is apparent that the pulse waveform from the time t(I)−(U+Zδ) to the time t(I) based on the above-described processing by the correlation coefficient calculating unit 18 is stable. During the duration, pulse of the number of n+1 occurs. The pulse wave detection unit 19 can therefore calculate the pulse rate h using the following Expression (23). If the pulse rate h is outside the possible range of the human pulse rate, e.g., 42 to 240 bpm, the pulse rate and the pulse waveform need not to be output. As another mode of the embodiment, the pulse wave detection unit 19 may output, for example, the pulse waveform from the time t(I)−(U+Zδ) to the time t(I).

$$h = 60/((U+Z\delta)/(n+1)) \text{ [bpm]} \qquad (23)$$

The pulse rate and the pulse waveform obtained as described above may be output to a not-illustrated display device included in the pulse wave detection apparatus 10 or any destination. For example, if a diagnostic computer program is installed in the pulse wave detection apparatus 10, the pulse rate and the pulse waveform may be output to the diagnostic computer program. The diagnostic computer program is used for diagnosing functions of the internal nerves based on the pulse rate and the fluctuation of the pulse period, or diagnosing cardiac diseases from the pulse waveforms. Alternatively, the pulse rate and the pulse waveform may be output to a server device, for example, that provides the diagnostic computer program as a Web service. Furthermore, the pulse rate and the pulse waveform may be output to a terminal device used by a person involved with a user of the pulse wave detection apparatus 10 such as a care worker and a doctor. This achieves a monitoring service that can be used outside the hospital, e.g., at home, or while sitting. It is needless to say that the measurement result or the diagnostics result of the diagnostic computer program is also displayed on the pulse wave detection apparatus 10 or other terminal device of the person involved.

The above-described units, i.e., the acquiring unit 13, the extraction unit 14, the waveform detecting unit 15, the transition determination unit 16a, the extreme value determination unit 16b, the window width setting unit 17a, the shift range setting unit 17b, the correlation coefficient calculating unit 18, and the pulse wave detection unit 19 can be implemented by a central processing unit (CPU) or a micro processing unit (MPU) performing a pulse wave detection computer program or a signal processing program. The above-described functions can also be implemented with a hardwired logic such as an application specific integrated circuit (ASIC) and a field programmable gate array (FPGA).

Semiconductor memory devices or storage devices may be adopted for the above-described internal memory. Examples of semiconductor memory devices include a video random access memory (VRAM), a random access memory (RAM), a read only memory (ROM), and a flash memory. Alternatively, storage devices such as a hard disk and an optical disk may be used rather than such memory devices.

Procedure of Processing

The following describes the procedure of the processing performed by the pulse wave detection apparatus according to the present embodiment. The waveform detection processing performed by the pulse wave detection apparatus 10 is firstly described (1), and then the waveform detection processing is described (2).

(1) Waveform Detection Processing

Figure 12:
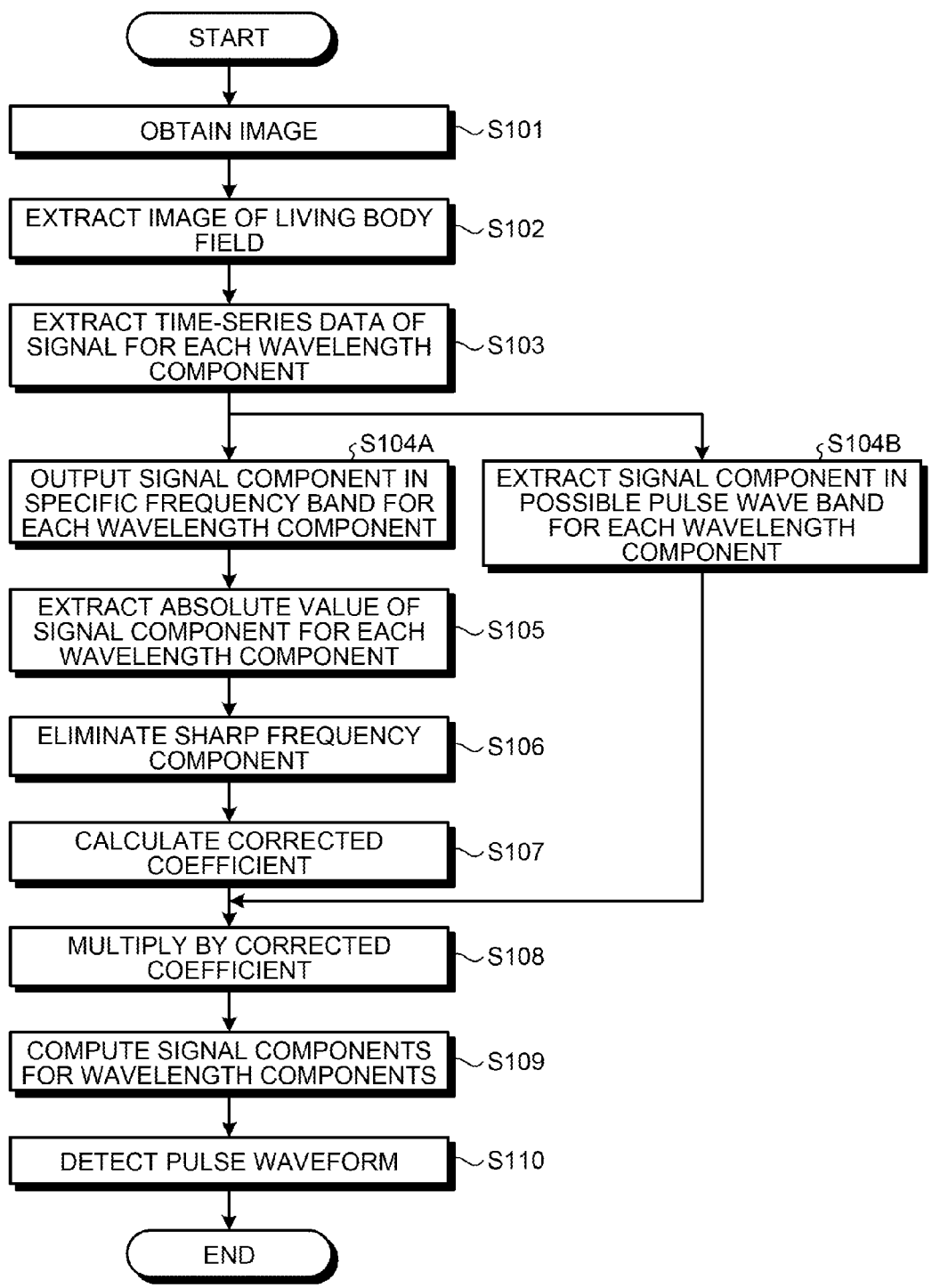
FIG. 12 is an exemplary diagram of a flowchart illustrating procedures of waveform detection processing according to the first embodiment.

FIG. 12 is an exemplary diagram of a flowchart illustrating procedures of the waveform detection processing according to the first embodiment. The waveform detection processing is started every time the camera 11 captures an image and repeated until no image is captured. If a stop operation is received through a not-illustrated input device, the waveform detection processing can be stopped.

As illustrated in FIG. 12, when an image including a subject is obtained (Step S101), the extraction unit 14 extracts an image of a living body field of the subject out of the images acquired at Step S101, for example, an image including a predetermined face part such as the nose of the subject (Step S102).

After that, the extraction unit 14 outputs the time-series data of the R signal to the BPF 152R and the BPF 156R and the time-series data of the G signal to the BPF 152G and the BPF 156G (Step S103).

Subsequently, the BPF 152R extracts a specific frequency band of the R signal, e.g., the signal component in the frequency band ranging from not less than 3 to less than 20 bpm. The BPF 152G extracts a signal component in a specific frequency band of the G signal (Step S104A).

The extraction unit 153R then extracts the absolute intensity value of the signal component in the specific frequency band of the R signal and the extraction unit 153G extracts the absolute intensity value of the signal component in the specific frequency band of the G signal (Step S105).

After that, the LPF 154R performs smoothing processing for response to the time change on the absolute intensity value of the time-series data of the specific frequency band of the R signal and the LPF 154G performs smoothing processing for response to the time change on the absolute intensity value of the time-series data of the specific frequency band of the G signal (Step S106).

Subsequently, the calculating unit 155 performs the division "$G'_{noise}/R'_{noise}$", that is, the absolute intensity $G'_{noise}$ in the specific frequency band of the G signal output by the LPF 154G is divided by the absolute intensity $R'_{noise}$ in the specific frequency band of the R signal output by the LPF 154R. As a result, the corrected coefficient a of the sensitivity difference is calculated (Step S107).

In parallel with the above-described processing at Step S104A, the BPF 156R extracts a signal component in the pulse wave frequency band of the R signal, for example, in the frequency band ranging from not less than 42 to less than 240 bpm and the BPF 156G extracts a signal component in the specific frequency band of the G signal (Step S104B).

After that, the multiplication unit 157 multiplies the signal component in the specific frequency band of the R signal extracted at Step S104B by the corrected coefficient a calculated at Step S107 (Step S108). The computing unit 158 then performs the subtraction "$a*R_{signal}-G_{signal}$" that is, the signal component in the specific frequency band of the G signal extracted at Step S104B is subtracted from the signal component in the specific frequency band of the R signal multiplied by the corrected coefficient a at Step S108 (Step S109).

The waveform detecting unit 15 outputs the time-series data of the computed signal as a pulse waveform to the transition determination unit 16a and the extreme value determination unit 16b (Step S110), and ends the processing.

(2) Correlation Coefficient Calculation Processing

Figure 13:
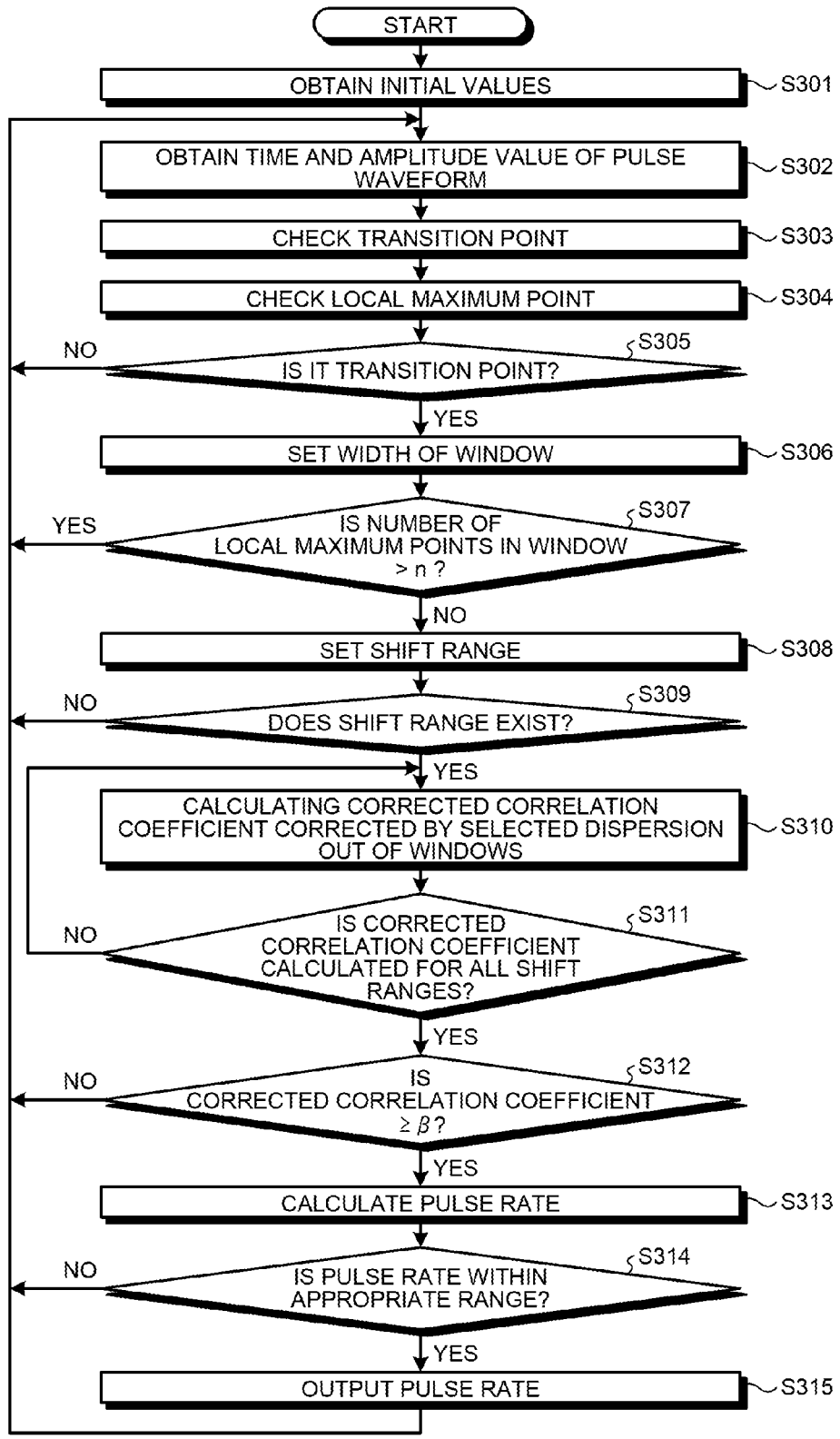
FIG. 13 is an exemplary diagram of a flowchart illustrating procedures of correlation coefficient calculation processing according to the first embodiment.

FIG. 13 is an exemplary diagram of a flowchart illustrating procedures of correlation coefficient calculation processing according to the first embodiment. The correlation coefficient calculation processing is repeated as long as the waveform detecting unit 15 inputs any pulse waveform.

As illustrated in FIG. 13, initial values for a the number of period of window n, the correlation coefficient threshold β, the coefficient of the shift range γ, for example, are obtained by respective functions from a not-illustrated internal memory (Step S301). After that, the transition determination unit 16a and the extreme value determination unit 16b obtain the time and the amplitude value of the pulse waveform from the waveform detecting unit 15 (Step S302).

The transition determination unit 16a determines whether the positive/negative of the amplitude value of the signal detected by the waveform detecting unit 15 transitions (Step S303). In addition, the extreme value determination unit 16b determines whether the amplitude value of a pulse waveform including the index preceded by one from the index at which the amplitude value of the pulse waveform is output is the maximum value (Step S304).

If the positive/negative of the amplitude value obtained at Step S302 transitions (Yes at Step S305), the window width setting unit 17a sets the length of the section backward in time from the transition point at which the positive/negative of the amplitude value is determined to transition until the number of transition points becomes equal to the number corresponding to the integral multiple of the period of the pulse wave, as the duration of the standard window (Step S306).

Subsequently, the shift range setting unit 17b determines whether the number of the local maximum points included in the standard window exceeds the number of the local maximum points corresponding to one period of the pulse wave (Step S307). On this occasion, if more local maximum points exist in the standard window than the number of the local maximum point corresponding to one period of the pulse wave (Yes at Step S307), measurement condition may be considered to be unstable. As a result, the shift range setting unit 17b does not perform the processing after this and the processing is proceeded to Step S302.

If the number of the local maximum points included in the standard window is equal to or less than the number of the local maximum points corresponding to one period of the pulse wave (No at Step S307), the shift range setting unit 17b multiplies the width of window U and the number of the period of window n in the standard window set at Step S306 by the coefficient of the shift range γ and concurrently multiplies the width of window U and the number of the period of window n by the reciprocal of the coefficient of the shift range γ, thereby setting the shift range w to the comparison window (Step S308).

If the shift range exists (Yes at Step S309), until the correlation coefficient calculating unit 18 calculates the corrected correlation coefficient for all of the shift indexes (No at Step S311) while incrementing the shift index z one by one from Zmin to Zmax, the correlation coefficient calculating unit 18 uses the above-described Expression (22) to select the larger dispersion out of the dispersions in the windows and uses it for division, thereby calculating the corrected correlation coefficient S(z) (Step S310).

After the corrected correlation coefficient S(z) is calculated for all of the shift indexes (Yes at Step S311), the correlation coefficient calculating unit 18 determines whether the corrected correlation coefficient S(z) is equal to or larger than the threshold β (Step S312). If the corrected correlation coefficient S(z) is smaller than the threshold β (No at Step S312), the correlation coefficient calculating unit 18 determines that a comparison window similar enough to the standard window has not been found. The correlation coefficient calculating unit 18 thus does not allow the pulse wave detection unit 19 to detect the pulse wave and the processing is returned to Step S302.

If the maximum value out of the corrected correlation coefficient S(Z) calculated at Step S310 is equal to or larger than the threshold β (Yes at Step S312), the pulse wave detection unit 19 calculates the pulse rate h using the above-described Expression (23) (Step S313). If the pulse rate h is outside the possible range of the human pulse rate, e.g., 42 to 240 bpm, (No at Step S314), the pulse wave detection unit 19 does not output the pulse rate and the pulse waveform and the processing is returned to Step S302.

If the pulse rate h is included in the possible range of the human pulse rate (Yes at Step S314), the pulse wave detection unit 19 outputs the pulse rate and the pulse waveform to a predetermined output destination (Step S315) and the pulse waveform and the processing is returned to Step S302.

Effects of First Embodiment

As described above, the pulse wave detection apparatus 10 according to the present embodiment performs signal processing of calculating the correlation coefficient, when determining the similarity of the waveforms using such a correlation coefficient value, in which the larger the difference between the dispersion of the amplitude value in the standard window and the dispersion of the amplitude value in the comparison window, the smaller the value of the correlation coefficient becomes. In the pulse wave detection apparatus 10 according to the present embodiment, therefore, the value of the correlation coefficient value is calculated to be low when the waveforms in the windows have a similarity relation to each other. With the pulse wave detection apparatus 10 according to the present embodiment, therefore, the accuracy of determination on the similarity of the waveforms can be improved.

[b] Second Embodiment

An embodiment of the disclosed signal processor has been described above, however, the present invention may be embodied in a variety of forms other than above-described embodiment. Therefore, another embodiment of the present invention will be described, hereinafter.

Application Example of Determination on Similarity

In the first embodiment, the correlation coefficient is used for determining the similarity of the waveforms, that is, the periodicity of the pulse wave. However, the index for determining the similarity of the waveforms is not limited to this example. For another example, the pulse wave detection apparatus 10 can use the following Expression (24) to calculate the Euclidean distance or use the following Expression (25) to calculate the normalized Euclidean distance. The shift range having the shortest distance out of all of the shift ranges is determined as the shift range Z having the highest periodicity. As described above, when the Euclidean distance or the normalized Euclidean distance is used, if the shortest distance thereof is larger than a predetermined threshold TH, the waveform in the standard window is not used for detecting pulse waves because the measurement condition is determined to be unstable.

$$S(z) = -\sqrt{\sum_{i=1}^{x} (x(i) - y(z, i))^2} \qquad (24)$$

$$S(z) = -\frac{\sqrt{\sum_{i=1}^{x} (x(i) - y(z, i))^2}}{\sqrt{\sum_{i=1}^{x} (x(i) - \overline{x})^2} \sqrt{\sum_{i=1}^{x} (y(z, i) - \overline{y(z)})^2}} \qquad (25)$$

Input Signal

In the above-described first embodiment and the second embodiment, two types of signals, i.e., the R signal and the G signal are used as input signals, however, the embodiments are not limited to this example. Any type of signal and any number of signal can be used as input signals as long as the signal has a plurality of different light wavelength components. For example, any combination of two signals having different light wavelength components out of R, G, B, IR, and NIR signals can be used. In addition, any combination of three or more of such signals can also be used.

Another Implementation

In the above-described first embodiment, the pulse wave detection apparatus 10 performs the above-described correlation coefficient calculation processing in a stand-alone configuration. However, the pulse wave detection apparatus 10 can also be implemented as a client server system. For example, the pulse wave detection apparatus 10 may be implemented as a Web server that performs the correlation coefficient calculation processing or as a cloud-based system that provide services such as a correlation coefficient calculation service through outsourcing. When the pulse wave detection apparatus 10 operates as a server device as described above, portable terminal devices such as a smart phone and a mobile phone or information processing device such as personal computer can be used as a client terminal. When an image including the face of a subject is obtained from such a client terminal through a network, the pulse wave detection apparatus 10 operating as a server device performs the waveform detection processing and uses the pulse waveform for performing the correlation coefficient calculation processing. The server device returns the detection result or a diagnostic result based on the detection result to the client terminal, whereby a pulse wave detection service and a diagnostic service can be provided.

Distribution and Integration

Furthermore, each of the elements of the devices illustrated in the drawings is merely a depiction of concepts or functionality, and does not always need to be configured physically in the manner illustrated in the drawings. In other words, specific configurations in which each of the devices is distributed or integrated are not limited to those illustrated in the drawings. More specifically, the whole or a part of the devices may be distributed or integrated functionally or physically in any unit depending on various loads or utilization. For example, the transition determination unit 16*a*, the extreme value determination unit 16*b*, the window width setting unit 17*a*, the shift range setting unit 17*b*, or the correlation coefficient calculating unit 18 may be coupled to the pulse wave detection apparatus 10 as an external device through a network. Alternatively, the transition determination unit 16a, the extreme value determination unit 16b, the window width setting unit 17a, the shift range setting unit 17b, or the correlation coefficient calculating unit 18 may be included in a separate device. More than one of them are coupled to each other through a network and cooperate with each other, thereby implementing the above-described functions of the pulse wave detection apparatus 10.

Signal Processing Program

The various types of processing described in the above-described embodiments may be achieved with computers such as a computer and a work station executing preliminary provided computer programs. The following describes an exemplary computer that performs a signal processing program having the same function as the above-described embodiment with reference to FIG. 14.

Figure 14:
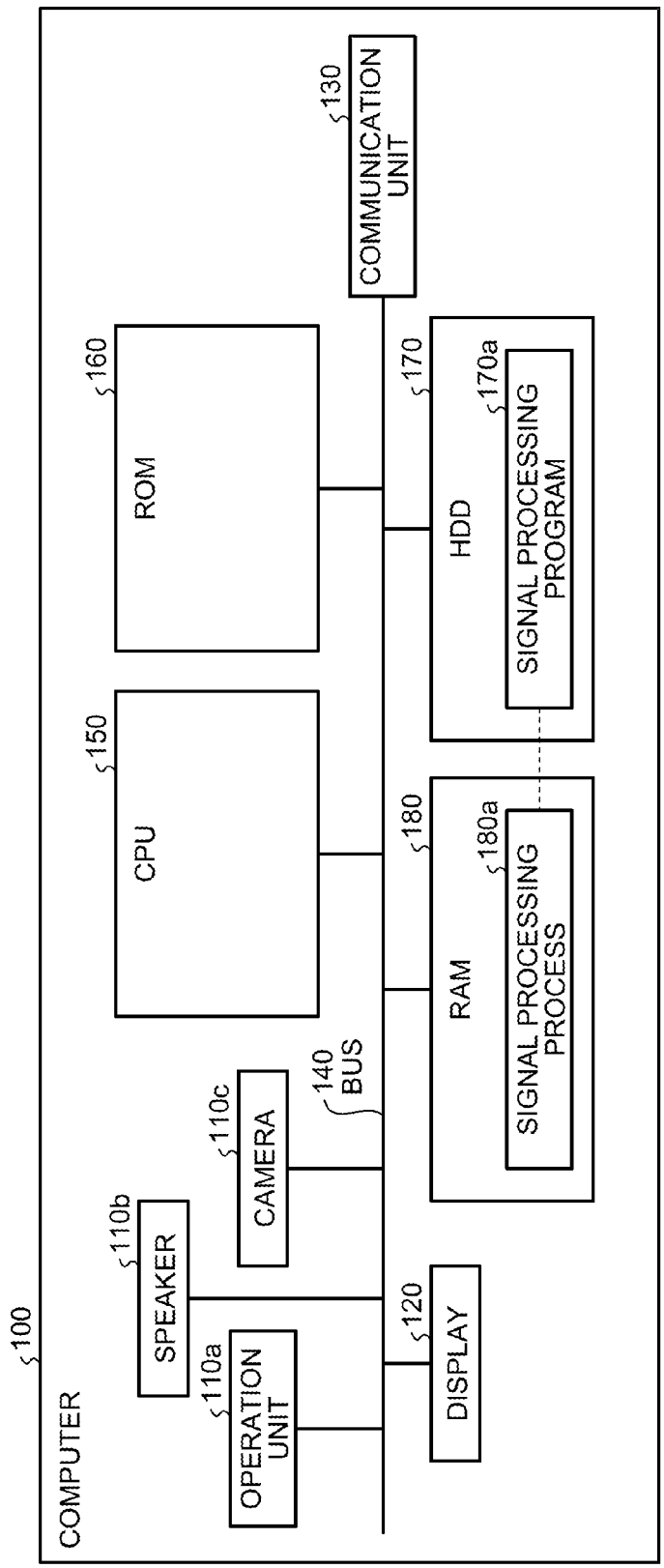
FIG. 14 is an explanatory diagram of an exemplary computer that executes a signal processing program according to the first embodiment and a second embodiment.

FIG. 14 is an explanatory diagram of an exemplary computer executing signal processing according to the first embodiment and the second embodiment. As illustrated in FIG. 14, a computer 100 includes an operation unit 110a, a speaker 110b, a camera 110c, a display 120, and a communication unit 130. The computer 100 includes a CPU 150, a ROM 160, an HDD 170, and a RAM 180. These units and components with numerals from 110 to 180 are coupled to each other through a bus 140.

In the HDD 170, as illustrated in FIG. 14, a signal processing program 170a is stored in advance that functions in the same manner as the transition determination unit 16a, the extreme value determination unit 16b, the window width setting unit 17a, the shift range setting unit 17b, and the correlation coefficient calculating unit 18 described in the first embodiment. The signal processing program 170a may also be distributed or integrated as appropriate in the same manner as the components illustrated in FIG. 1, such as the transition determination unit 16a, the extreme value determination unit 16b, the window width setting unit 17a, the shift range setting unit 17b, and the correlation coefficient calculating unit 18. In other words, not all pieces of data are stored in the HDD 170. Only the pieces of data used for the processing may be stored in the HDD 170.

The CPU 150 reads the signal processing program 170a from the HDD 170 and loads the program to the RAM 180. This enables the signal processing program 170a to function as a signal processing process 180a as illustrated in FIG. 14. The signal processing process 180a then loads the pieces of data read by the HDD 170 to the corresponding fields allocated on the RAM 180 as appropriate and performs the various types of processing based on the loaded pieces of data. The signal processing process 180a includes the various types of processing performed in the transition determination unit 16a, the extreme value determination unit 16b, the window width setting unit 17a, the shift range setting unit 17b, and the correlation coefficient calculating unit 18 illustrated in FIG. 1, such as the processing illustrated in FIGS. 12 and 13. In addition, not all processing units implemented virtually on the CPU 150 are operated on the CPU 150, and only the pieces of processing units used for the processing may be implemented.

Incidentally, the image processing programs described above need not to be stored in the HDD 170 and the ROM 160 from the beginning. For example, the image processing programs are stored in "portable physical media" inserted in the computer 100 such as a flexible disk (FD), a compact disk read-only memory (CD-ROM), a digital versatile disk (DVD), a magneto-optical disk, and an IC card. The computer 100 may retrieve the programs from the portable physical media and execute them. Additionally, a server device or any other computer coupled to the computer 100 through a public line, the Internet, LAN, and WAN, may store therein the computer programs. In this case, the computer 100 may retrieve the programs from the server device or any other computer and execute them.

According to an embodiment of the present invention, the accuracy of determination on the similarity of waveforms may be improved.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A signal processor comprising:
a memory; and
a processor coupled to the memory, wherein the processor executes a process comprising:
   detecting a signal;
   calculating a correlation coefficient between waveforms of the signal included in a first window and a second window having a predetermined duration;
   correcting the correlation coefficient such that the larger a difference between dispersion of the amplitude value in the first window and dispersion of the amplitude value in the second window becomes, the smaller the correlation coefficient becomes, by selecting a larger dispersion out of the dispersion in the first window and the dispersion in the second window and using the selected dispersion by a following equation:

$$S(z) = \frac{\sum_{i=1}^{x}(x(i)-\bar{x})(y(z,i)-\overline{y(z)})}{\max\left(\sum_{i=1}^{x}(x(i)-\bar{x})^2, \sum_{i=1}^{x}(y(z,i)-\overline{y(z)})^2\right)}$$

S representing the correlation coefficient,
i representing the index of a pulse waveform,
x representing a value of the pulse waveform included in the first window,
y representing a value of the pulse waveform included in the second window, and
z representing a shift index; and
detecting a pulse waveform when the corrected correlation coefficient is equal to or larger than a predetermined threshold, wherein
the detecting includes detecting the signal in a frequency band corresponding to a pulse wave from an image in which a living body has been captured, so that fluctuation of volume of blood associated with the pulse wave of a subject is detected using an image in which the subject is captured under typical ambient light, without contacting a measuring instrument with the living body of the subject, and the calculating includes calculating the correlation coefficient between waveforms in the first window and the second window using the signal detected at the detecting, wherein the process further comprises:

first setting the duration of the first window; and second setting a range used for shifting the second window from the first window, and wherein the calculating includes calculating the correlation coefficient between a waveform in the first window of which duration is set at the first setting and a waveform in the second window shifted from the first window twice or more times within the range set at the second setting, wherein the correlation coefficient is an index indicating that the larger a value, the more similar are the pulse waveform in a standard window and the pulse waveform in a comparison window shifted from the standard window.

2. The signal processor according to claim 1, wherein the process further comprises:

transition determining whether the positive and negative of the amplitude value of the signal transitions to determine a transition point at which the positive and negative of the amplitude value transitions, and wherein the first setting includes setting the duration of the first window to a duration containing transition points the number of which corresponds to the integral multiple of a cycle of the pulse wave.

3. The signal processor according to claim 1, wherein the process further comprises:

determining whether the amplitude value of the signal is an extreme value, and wherein the second setting includes setting of the range when the number of the local maximum points included in the first window out of the local maximum points determined as the local maximum at the determining is equal to the number corresponding to the cycle of the pulse wave.

4. The signal processor according to claim 1, wherein the second setting includes setting the range using the duration set to the first window at the first setting.

5. A signal processing method comprising:

detecting, using a processor, a signal;

calculating, using the processor, a correlation coefficient between waveforms of the signal included in a first window and a second window having a predetermined duration;

correcting, using the processor, the correlation coefficient such that the larger a difference between dispersion of the amplitude value in the first window and dispersion of the amplitude value in the second window becomes, the smaller the correlation coefficient becomes, by selecting a larger dispersion out of the dispersion in the first window and the dispersion in the second window and using the selected dispersion by a following equation:

$$S(z) = \frac{\sum_{i=1}^{x}(x(i)-\bar{x})(y(z,i)-\overline{y(z)})}{\max\left(\sum_{i=1}^{x}(x(i)-\bar{x})^2, \sum_{i=1}^{x}(y(z,i)-\overline{y(z)})^2\right)}$$

S representing the correlation coefficient, i representing the index of a pulse waveform, x representing a value of the pulse waveform included in the first window, y representing a value of the pulse waveform included in the second window, and z representing a shift index; and detecting a pulse waveform when the corrected correlation coefficient is equal to or larger than a predetermined threshold, wherein the detecting includes detecting the signal in a frequency band corresponding to a pulse wave from an image in which a living body has been captured, so that fluctuation of volume of blood associated with the pulse wave of a subject is detected using an image in which the subject is captured under typical ambient light, without contacting a measuring instrument with the living body of the subject, and the calculating includes calculating the correlation coefficient between waveforms in the first window and the second window using the signal detected at the detecting, wherein the signal processing method further comprises:

first setting the duration of the first window; and second setting a range used for shifting the second window from the first window, and wherein the calculating includes calculating the correlation coefficient between a waveform in the first window of which duration is set at the first setting and a waveform in the second window shifted from the first window twice or more times within the range set at the second setting, wherein the correlation coefficient is an index indicating that the larger a value, the more similar are the pulse waveform in a standard window and the pulse waveform in a comparison window shifted from the standard window.

6. A non-transitory computer readable recording medium having stored therein a signal processing program that causes a computer to execute a process comprising:

detecting a signal;

calculating a correlation coefficient between waveforms of the signal included in a first window and a second window having a predetermined duration;

correcting the correlation coefficient such that the larger a difference between dispersion of the amplitude value in the first window and dispersion of the amplitude value in the second window becomes, the smaller the correlation coefficient becomes, by selecting a larger dispersion out of the dispersion in the first window and the dispersion in the second window and using the selected dispersion by a following equation:

$$S(z) = \frac{\sum_{i=1}^{x}(x(i)-\bar{x})(y(z,i)-\overline{y(z)})}{\max\left(\sum_{i=1}^{x}(x(i)-\bar{x})^2, \sum_{i=1}^{x}(y(z,i)-\overline{y(z)})^2\right)}$$

S representing the correlation coefficient, i representing the index of a pulse waveform, x representing a value of the pulse waveform included in the first window, y representing a value of the pulse waveform included in the second window, and z representing a shift index; and detecting a pulse waveform when the corrected correlation coefficient is equal to or larger than a predetermined threshold, wherein the detecting includes detecting the signal in a frequency band corresponding to a pulse wave from an image in which a living body has been captured, so that fluctuation of volume of blood associated with the pulse wave of a subject is detected using an image in which the subject is captured under typical ambient light, without contacting a measuring instrument with the living body of the subject, and the calculating includes calculating the correlation coefficient between waveforms in the first window and the second window using the signal detected at the detecting, wherein the process further comprises:

first setting the duration of the first window; and second setting a range used for shifting the second window from the first window, and wherein the calculating includes calculating the correlation coefficient between a waveform in the first window of which duration is set at the first setting and a waveform in the second window shifted from the first window twice or more times within the range set at the second setting, wherein the correlation coefficient is an index indicating that the larger a value, the more similar are the pulse waveform in a standard window and the pulse waveform in a comparison window shifted from the standard window.

* * * * *